United States Patent
Mehmet

(10) Patent No.: US 8,382,473 B2
(45) Date of Patent: Feb. 26, 2013

(54) APPARATUS AND METHOD RELATING TO TEETH WHITENING

(76) Inventor: Ahmet E. Mehmet, London (GB)

( * ) Notice: Subject to any disclaimer, the term of this patent is extended or adjusted under 35 U.S.C. 154(b) by 459 days.

(21) Appl. No.: 11/712,837

(22) Filed: Feb. 28, 2007

(65) Prior Publication Data

US 2007/0212661 A1 Sep. 13, 2007

(30) Foreign Application Priority Data

Mar. 1, 2006 (GB) .................................. 0604167.7

(51) Int. Cl.
*A61C 3/00* (2006.01)
*A61C 9/00* (2006.01)

(52) U.S. Cl. ........................................... 433/32; 433/35

(58) Field of Classification Search .................. 433/216, 433/32–37, 80, 89; 607/96–114; 606/27–31
See application file for complete search history.

(56) References Cited

U.S. PATENT DOCUMENTS

| 4,308,013 A * | 12/1981 | Major ............................... 433/32 |
| 5,136,850 A * | 8/1992 | Bierschenk et al. ............ 62/3.62 |
| 6,402,739 B1 | 6/2002 | Neev |
| 2001/0012608 A1 * | 8/2001 | Darnell ........................... 433/216 |
| 2001/0038998 A1 * | 11/2001 | Lindquist ........................ 433/215 |
| 2006/0003284 A1 | 1/2006 | Sale et al. |

FOREIGN PATENT DOCUMENTS

| EP | 10262991 | * 10/1998 |
| FR | 2571250 | 10/1984 |
| GB | 2416311 | 1/2006 |
| JP | 11-004839 | 1/1989 |
| JP | 10-262991 | 10/1998 |
| WO | 01/85052 | 11/2001 |

* cited by examiner

*Primary Examiner* — Yogesh Patel

(74) *Attorney, Agent, or Firm* — Renner, Otto, Boisselle & Sklar, LLP

(57) ABSTRACT

A teeth whitening apparatus and a method of teeth whitening is provided. The apparatus includes one or more thermoelectric device(s) which may be in the form of peltier devices adapted to be placed in the mouth. The or each thermoelectric device has one side that heats up and another side that is cooled when an electrical current is passed through the or each device. The or each thermoelectric device is preferably molded into a mouth guard into which a teeth whitening composition is placed such that the heat generated by the or each thermoelectric device activates the teeth whitening composition. The one or more thermoelectric device(s) are preferably powered by one or more batteries. Preferably, the one or more thermoelectric device(s) are coupled to one or more heat sinks such that the heat produced by the one or more thermoelectric device(s) is spread out over the teeth to be whitened.

15 Claims, 1 Drawing Sheet

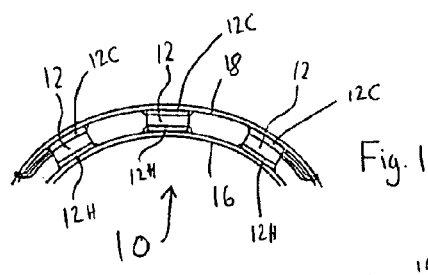
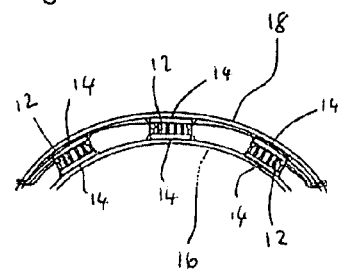
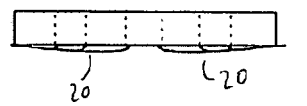
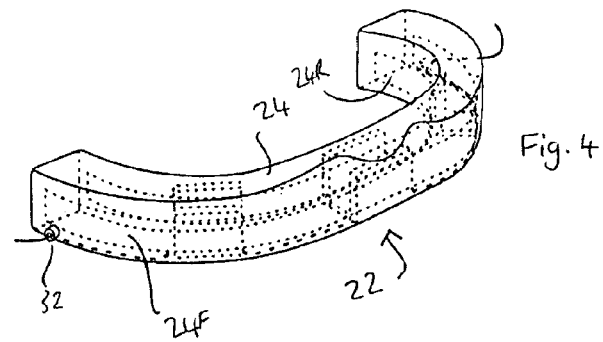
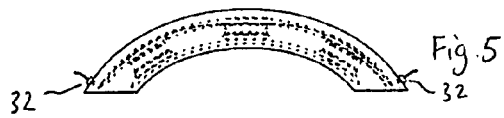
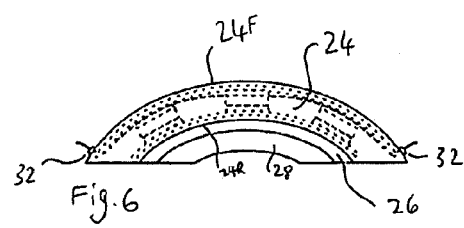
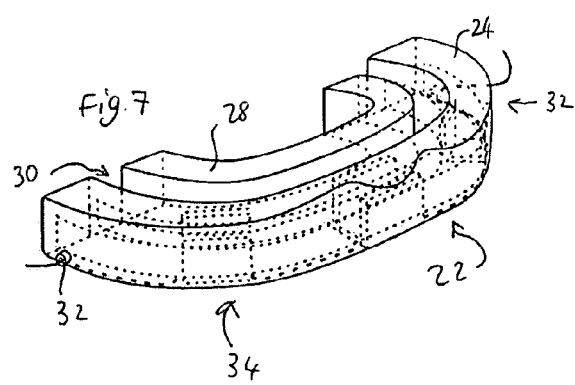

APPARATUS AND METHOD RELATING TO TEETH WHITENING

RELATED APPLICATIONS

This application claims the benefit of United Kingdom Patent Application No. 0604167.7, filed Mar. 1, 2006, which is incorporated by reference herewith in its entirety.

FIELD OF INVENTION

The present invention relates to an apparatus and method to aid teeth whitening and particularly, but not exclusively, relates to a device to provide heat to increase the rate of activation of a tooth whitening composition.

BACKGROUND

Conventionally, in order to whiten a patients' teeth in a dental surgery, dentists apply bleach (usually containing or consisting of Hydrogen Peroxide ($H_2O^2$)) to the teeth and will direct laser light at the bleach in order to activate it to increase the rate at which the bleach whitens the teeth. However, this conventional method of whitening teeth can only be conducted within a dental surgery due to its inherent dangers and therefore this conventional method is relatively expensive.

Another conventional method for whitening teeth involves a user self-applying a whitening toothpaste or dentifrice containing hydrogen peroxide (or another composition with an equivalent bleaching effect) within a gel or paste which has an effect of releasing between 0.1% and 3% of hydrogen peroxide ($H_2O^2$) (or the equivalent of between 0.1% and 3% of hydrogen peroxide if another bleach or cleaning agent were used.) However, this conventional self-application method suffers from the disadvantage that it is slower to use; alternatively, higher levels of bleach/$H_2O^2$ can be used in order to achieve a higher activation rate but high levels can be dangerous to the teeth and indeed general health of the user.

SUMMARY

It is an aim of the present invention to provide a method and device for increasing the rate of activation of a tooth whitening composition in order to increase the convenience of a user who wishes to self-applicate the whitening/bleaching cleaning dentifrice or paste.

According to the present invention there is provided a teeth whitening apparatus comprising:
  one or more thermoelectric device(s) adapted to be placed in the mouth, the or each thermoelectric device comprising one side that heats up and another side that is cooled when an electrical current is passed through the or each device.

According to the present invention there is provided a method of teeth whitening comprising:
  providing a whitening composition in close proximity or into contact with the teeth to be whitened;
  inserting one or more thermoelectric device(s) into the mouth; and
  passing an electrical current through the or each device such that one side in close proximity to or in contact with the whitening composition heats up and another side of the or each device cools down.

Preferably, the apparatus further comprises a power supply electrically connected to said one or more thermoelectric device(s), wherein actuation of the power supply causes current to pass through the or each device. Typically, the voltage applied to the one or more devices is in the range 0.8V to 1.5V.

Typically, the one or more thermoelectric device(s) are arranged such that, in use, the one side that heats up is facing toward the face of the teeth to be whitened and the other side that is cooled is facing away from the face of the teeth to be whitened.

Preferably, the apparatus further comprises a heat conductive material which more preferably comprises a heat sink and most preferably the one or more thermoelectric device(s) are coupled to the heat sink such that the heat produced by the one or more thermoelectric device(s) is spread out over the teeth to be whitened. Preferably, the heat sink comprises a pair of heat conductive strips, wherein one strip is coupled to the said side that heats up and the second strip is coupled to the side that is cooled.

Preferably, the pair of heat conductive strips are coupled to the respective sides of the one or more thermoelectric devices by a fixing means which may comprise an adhesive or, more preferably, a conductive epoxy resin.

Preferably, the apparatus further comprises a mouth guard, wherein the mouth guard is typically moulded around the pair of heat conductive strips, the fixing means and the one or more thermoelectric devices.

Preferably, the mouth guard comprises a front wall, the inner face of which is adapted in use to contact the front face of the teeth, a bridge portion which is adapted in use to contact the biting edge of the teeth and a rear wall, the inner face of which is adapted in use to contact the rear face of the teeth. More preferably, the pair of heat conductive strips, the fixing means and the one or more thermoelectric devices are moulded into the front wall of the mouth guard.

Optionally, another pair of heat conductive strips, fixing means and one or more thermoelectric devices may be moulded into the rear wall of the mouth guard should the rear face of the teeth require to be whitened.

Preferably, the one or more thermoelectric devices are peltier devices. Preferably, the or each peltier device comprises one side that heats up and another side that is cooled when a direct current (dc) is passed through the or each device. The peltier devices act to transfer heat from the cool side to the hot side when the dc current passes through in one direction. Accordingly, when more than one peltier devices are provided, the peltier devices are arranged with their polarity aligned in the same direction.

Typically, the power supply comprises a dc power supply which is preferably one or more battery(ies) and more preferably is one or more 1.5V 'AAA' or other small sized batteries arranged in series.

Typically, the peltier devices are connected to the dc power supply via a pair of wires and, when more than one peltier devices are provided, are arranged to connect in parallel to the dc power supply. Preferably, the wires leading from the peltier devices terminate in a wire coupling point provided at one or both sides of the mouth guard, wherein a pair of wires leading from the battery can be plugged into one of the wire coupling points.

BRIEF DESCRIPTION OF THE DRAWINGS

Embodiments of the present invention will now be described, by way of example only, with reference to the accompanying drawings, in which:

FIG. 1 is a plan view (from above) of an apparatus in accordance with the present invention, with the mouth guard emitted for clarity;

FIG. 2 is a plan view (from below) of the apparatus of FIG. 1;

FIG. 3 is a front view of the apparatus of FIG. 1;

FIG. 4 is a perspective view of the apparatus of FIG. 1 moulded into the front wall of a mouth guard but with the rest of the mouth guard omitted for clarity;

FIG. 5 is a plan view from below of the apparatus of FIG. 4;

FIG. 6 is a plan view from above of the apparatus of FIG. 4, but with a bridge portion and rear wall of the mouth guard also being shown; and FIG. 7 is a perspective view of the apparatus of FIG. 6.

DETAILED DESCRIPTION

FIG. 1 shows an apparatus 10 prior to being moulded into a mouth guard as comprising three thermoelectric devices, in the form of peltier devices 12, sandwiched between a pair of conductive heat sink strips 16, 18.

The polarity of the peltier devices 12 is arranged such that when they are connected to a power supply (not shown) and DC current is passed through the peltier devices 12, heat moves from the cold side 12C to the hot side 12H of the peltier devices 12. The cold sides 12C of the peltier devices 12 are connected to an outer (cold) heat sink strip 18 and the hot side 12H of the peltier devices 12 are connected to an inner (hot) heat sink strip 16. The hot 12H and cold 12C sides are connected to the respective heat sink strips 16, 18 via a suitable fixing means such as an epoxy resin 14 which hardens when heated, although any other suitable fixing means such as screws, clamps or another form of adhesive etc. could be used if suitable.

The peltier devices 12 are the preferred thermo-electric devices since peltier devices can be operated by using a relatively low DC current which can be provided by e.g. one or two 1.5 volt AAA batteries (not shown). This provides great safety advantages and also a much improved user friendly operation over conventional teeth whitening techniques. Examples of suitable peltier devices are Miniature Modules manufactured by Supercool AB of Sweden under Product number PE-011-05-15 which are 2.5 mm by 2.5 mm in size and have a maximum rating of 0.8 A and 1.4V. However, other peltier devices 12 could be used if suitable.

The batteries are preferably provided in a control pack (not shown) which further comprises a controller (not shown) including a power module (not shown). A suitable power module is an Auto-track™ power module produced by Astec of Carlsbad, Calif. under product number ATH06T033-9(J); in this case, four 'AAA' batteries are preferred, split into pairs in parallel with both pairs arranged in series, such that the power module is supplied with 3V and can output Voltage in the range of 0.8V to 1.5V depending on the output switch selected by the user. The control pack is arranged with suitable switches to allow a user or a dentist to adjust the voltage delivered to the peltier devices such that, for example:

a) this setting provides an in mouth temperature of 55 degrees for 15 minutes; or b) this setting provides an in mouth temperature of 50 degrees for 30 minutes.

Other settings can be provided if desired. For instance, a high temperature setting (e.g. up to 70 degrees) and a reverse setting could be provided (in which the polarity of the peltier devices is reversed in order to reverse the flow of temperature) if it was desired to provide the option of moulding the mouthguard 22 to fit a particular users mouth and teeth. In this instance, the dentist would insert the mouthguard 22 into the users mouth and set the switch (not shown) to the high temperature setting and within a few seconds the thermo-plastic would transform from being opaque to transparent/clear (which indicates the thermo-plastic is now soft and can be moulded to take the form of the users mouth). The dentist, seeing the transformation would then flick the switch to the reverse setting which then very quickly cools the rear face 24R and thus sets the thermo-plastic mouthguard to fix the moulding to that of the users mouth and teeth. Alternatively, the high temperature setting could be omitted with that step replaced by placing the mouthguard 22 into hot (i.e. 70 degrees) water until the mouthguard 22 turns transparent.

The inner and outer heat sink strips 16, 18 can be formed from any heat conductive material that is, preferably, inert and non-corrosive such as aluminium (which is preferably coated with gold or platinum to prevent oxidisation of the aluminium) and the heat sink strips 16, 18 are relatively thin, being in the region of 0.5 mm thick or less. The heat sink strips 16, 18 have the advantage that they spread out the heat (and cooling effect) produced by the peltier devices 12 over the teeth to be whitened.

The apparatus 10 is connected to the batteries via the wires 20 (shown most clearly in FIG. 3) and could be used as shown in FIGS. 1-3 by coating the inner face of the inner heat sink strip 16 with the whitening gel/paste/toothpaste (or other whitening composition) containing the active bleaching ingredient. The user would then place the apparatus 10 into the mouth with the inner heat sink strip 16 and whitening composition pressed into contact with the teeth to be whitened, typically the upper left incisor to upper right incisor. However, it is envisaged that it will be preferable to mould the apparatus 10 into a mouth guard or gum shield formed from a thermo-plastic material.

FIG. 4 shows the apparatus 10 being moulded into the front wall 24 of a mouth guard/gum shield. Again, the mouth guard 22 comprising only the front wall 24 could be used as shown in FIG. 4 with the whitening composition containing the active bleaching ingredient being applied onto the rear most face 24R, with the rear most face 24R being inserted into the mouth and placed into contact with the front of the teeth to be whitened.

However, it is envisaged that it will likely be of most benefit to a user if the mouth guard 22 also comprises a rear wall 28, with the rear wall 28 and the front wall 24 being connected via a bridge portion 26, as shown in FIGS. 6 and 7. In this case, the user would spread the whitening composition containing the active bleaching ingredient into the trough 30 of the U-shaped mouth guard 22 as shown in FIG. 7 and the user would place the mouth guard 22 into their mouth with their teeth biting into the trough 30. When the battery (not shown) is connected to one of the wire coupling points 32 (which in turn are suitably wired to each of the peltier devices 12), the rear face 24R of the front wall 24 will heat up, typically up to 50-55° C. and the heat will increase the rate at which the whitening composition containing the active bleaching ingredient whitens the teeth.

Furthermore, the front face 24F will be cooled by its close proximity to the outer heat sink strip 18 and therefore will keep the inside of the lip of the user cool and thus provides a safety benefit.

Optionally, a second apparatus 10 could be moulded into the rear wall 28 if a person wished to whiten the rear of their teeth; however, it is more usual for users to only wish to whiten the front of their teeth in which case the second apparatus 10 can be omitted from the rear wall 28 and indeed the rear wall 28 can be made much thinner than that shown in FIG. 7.

It should be noted that a persons mouth, including their tongue, is less sensitive than e.g. a persons hand or face and a persons mouth will not experience any discomfort up to approximately 50-55° C.

A person would likely use the apparatus 10 or 22 for 15, 30 or 45 minutes per session depending upon the temperature chosen and could use the apparatus 10, 22 once a day if the percentage of active hydrogen peroxide (or equivalent) within the whitening composition is less than 1%. It should be noted that the gum shield 22 could be any inert material and is also preferably a high density material. Furthermore, a user could connect the battery to either of the wire coupling points 32 and this feature provides added usability. Furthermore, it should be noted that the apparatus 10 or 22 could be used on either the upper teeth or lower teeth, but in practice it is likely that a person will use it on the upper teeth since it is normally more important to whiten the upper teeth.

Accordingly, with the peltier devices being relatively thin in the region of 2.5 mm thick and the heat sink being 0.5 mm or less in thickness, the mouth guard front wall thickness could be in the region of only an additional 1 mm thick and therefore the gum shield 22 is likely to be relatively thin overall.

A preferred whitening composition for use with the apparatus 10, 22 is the Opale™ whitening toothpaste or the Diamond™ whitening toothpaste, the Janina Ultra White or Janina Ultra White+, all products produced by Janina International Limited of London, United Kingdom.

Modifications and improvements may be made to the embodiments described hereinbefore without departing from the scope of the invention. For example, less than three peltier devices 12 could be used, particularly if a user wished only to whiten one or two teeth. For instance, only one peltier device 12 could be used if a person was only wishing to whiten e.g. the front two teeth.

The invention claimed is:

1. Teeth whitening apparatus, comprising:
   a thermoelectric device adapted to be placed in the mouth, the thermoelectric device comprising one side that heats up and another side that is cooled when an electrical current is passed through the thermoelectric device;
   a heat sink adapted to be placed in the mouth along the teeth to be whitened and comprising a pair of heat conductive strips, wherein one strip when in use faces the teeth to be whitened and is coupled to the side of the thermoelectric device that heats up, and the other strip is coupled to the other side of the thermoelectric device away from the face of the teeth to be whitened; and
   a mouth guard, wherein the mouth guard is molded around the pair of heat conductive strips and the thermoelectric device.

2. Apparatus according to claim 1, further comprising: a power supply electrically connected to the thermoelectric device, wherein actuation of the power supply causes current to pass through the thermoelectric device.

3. Apparatus according to claim 2, wherein the power supply applies a voltage to the thermoelectric device in the range 0.8V to 1.5V.

4. Apparatus according to claim 1, wherein the pair of heat conductive strips are coupled to the respective sides of the thermoelectric device by a fixing member.

5. Apparatus according to claim 4, wherein the mouth guard is molded around the fixing member.

6. Apparatus according to claim 5, wherein the mouth guard comprises a front wall, an inner face of the front wall is adapted in use to contact front face of the teeth, a bridge portion which is adapted in use to contact a biting edge of the teeth and a rear wall, an inner face of the rear wall is adapted in use to contact rear face of the teeth.

7. Apparatus according to claim 6, wherein the pair of heat conductive strips, the fixing member and the thermoelectric device are molded into the front wall of the mouth guard.

8. Apparatus according to claim 7, wherein another pair of heat conductive strips, a fixing member and a thermoelectric device are molded into the rear wall of the mouth guard.

9. Apparatus according to claim 8, wherein the thermoelectric device is a peltier device.

10. Apparatus according to claim 9, wherein the peltier device comprises one side that heats up and another side that is cooled when a direct current (dc) is passed through the peltier device.

11. Apparatus according to claim 10, wherein the power supply comprises a dc power supply.

12. Apparatus according to claim 11, wherein the power supply comprises a battery.

13. Apparatus according to claim 12, wherein the peltier device is connected to the dc power supply via a pair of wires, and, when more than one peltier device is provided, are arranged to connect in parallel to the dc power supply.

14. Apparatus according to claim 13, wherein the wires leading from the peltier device each terminate in a wire coupling point provided at one or both sides of the mouth guard, wherein a pair of wires leading from the battery are adapted to be plugged into the wire coupling points.

15. A method of teeth whitening, comprising the steps of: providing a whitening composition in close proximity or into contact with the teeth to be whitened;
   inserting a teeth whitening apparatus into the mouth, the teeth whitening apparatus including a thermoelectric device adapted to be placed in the mouth, the thermoelectric device comprising one side that heats up and another side that is cooled when an electrical current is passed through the thermoelectric device, and a heat sink adapted to be placed in the mouth along the teeth to be whitened and comprising a pair of heat conductive strips, wherein one strip faces the teeth to be whitened and is coupled to the side of the thermoelectric device that heats up, and the other strip is coupled to the other side of the thermoelectric device away from the face of the teeth to be whitened;
   and passing an electrical current through the thermoelectric device such that the one strip facing the teeth heats up and the other strip cools down.

* * * * *